US012746194B2

(12) United States Patent
Chapman et al.

(10) Patent No.: US 12,746,194 B2
(45) Date of Patent: Sep. 29, 2026

(54) DEODORANT

(71) Applicant: Java Beard, LLC, Manasquan, NJ (US)

(72) Inventors: Brad S. Chapman, Brielle, NJ (US); Jennifer Paige Chapman, Brielle, NJ (US); Brad J. Chapman, Brielle, NJ (US); Quinn H. Chapman, Brielle, NJ (US); Kane R. Chapman, Brielle, NJ (US)

(73) Assignee: Java Beard, LLC

( * ) Notice: Subject to any disclaimer, the term of this patent is extended or adjusted under 35 U.S.C. 154(b) by 0 days.

(21) Appl. No.: 19/055,601

(22) Filed: Feb. 18, 2025

(65) Prior Publication Data

US 2025/0262144 A1 Aug. 21, 2025

Related U.S. Application Data

(60) Provisional application No. 63/555,847, filed on Feb. 20, 2024.

(51) Int. Cl.
*A61K 8/92* (2006.01)
*A61Q 15/00* (2006.01)

(52) U.S. Cl.
CPC .............. *A61K 8/922* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 9,358,191 B2 | 6/2016 | Hiramoto et al. | |
| 2004/0037792 A1 | 2/2004 | Hiramoto et al. | |
| 2016/0355456 A1* | 12/2016 | Toyohara | C07C 69/732 |
| 2019/0000736 A1* | 1/2019 | Sturgis | A61K 8/44 |
| 2022/0339087 A1* | 10/2022 | Lindsay | A61K 8/891 |

FOREIGN PATENT DOCUMENTS

| | | |
|---|---|---|
| KR | 20180055303 A | 5/2018 |
| WO | WO 2022/192215 | 3/2022 |

OTHER PUBLICATIONS

Saud, Shah, and Ahmad Mohammad Salamatullah. "Relationship between the Chemical Composition and the Biological Functions of Coffee." Molecules (Basel, Switzerland), vol. 26, No. 24, 2021, pp. 7634-7647, https://doi.org/10.3390/molecules26247634.
Hurtado-Benavides, Andrés et al. "Study of the fatty acid profile and the aroma composition of oil obtained from roasted Colombian coffee beans by supercritical fluid extraction." Journal of Supercritical Fluids 113 (2016): 44-52.

* cited by examiner

*Primary Examiner* — Celeste A Roney
(74) *Attorney, Agent, or Firm* — Moser Taboada

(57) ABSTRACT

A coffee oil extract composition is disclosed, along with a composition having deodorant properties comprising an oil extract of roasted coffee beans. A method of making the composition is also disclosed.

16 Claims, 3 Drawing Sheets

DEODORANT

FIELD

The instant disclosure is generally directed to personal hygiene compositions, more particularly, to deodorant compositions, components of deodorant compositions, and methods for producing the same.

BACKGROUND

Deodorants are used to eliminate or reduce malodors. Numerous deodorant compositions exist, both comprising synthetic components and all-natural compositions.

However, deodorant technology appears to be insufficient in deodorizing effect.

The inventors have discovered a deodorant composition with greatly improved properties over known deodorant compositions.

SUMMARY

The present summary is provided to introduce a selection of concepts that are further described below in the detailed description. The present summary is not intended to identify key or essential features of the claimed subject matter, nor to be used as an aid in limiting the scope of the claimed subject matter. In embodiments, a composition having deodorant properties comprises an oil extract of roasted coffee beans.

In embodiments, a method of making a composition having deodorant properties, comprises contacting roasted coffee beans with an oil at a temperature and for a period of time sufficient to extract one or more components from the roasted coffee beans, and separating at least a portion of the roasted coffee beans from the oil to produce a coffee oil extract; combining the coffee oil extract with one or more of another oil, a butter, a wax, or a thickener at a temperature above each of the oil, butter, or wax present, to produce the composition.

In embodiments, a method of producing a coffee oil extract, comprises masticating a plurality of roasted coffee beans; contacting the masticated roasted coffee beans with an extraction solvent comprising fractionated coconut oil at a temperature from about 12° C. to about 53° C., and for a period of time from about 0.5 hours to 72 hours; and separating at least a portion of the masticated roasted coffee beans from the extraction solvent.

BRIEF DESCRIPTION OF THE DRAWINGS

So that the manner in which the above recited features of embodiments of the instant disclosure can be understood in detail, a more particular description of the embodiments, briefly summarized above, may be had by reference to embodiments, some of which are illustrated in the appended drawing. However, the appended drawing illustrates only an embodiment of the disclosure, and is therefore not to be considered limiting of scope, for the disclosure may admit to other equally effective embodiments.

DETAILED DESCRIPTION

Figure 1:
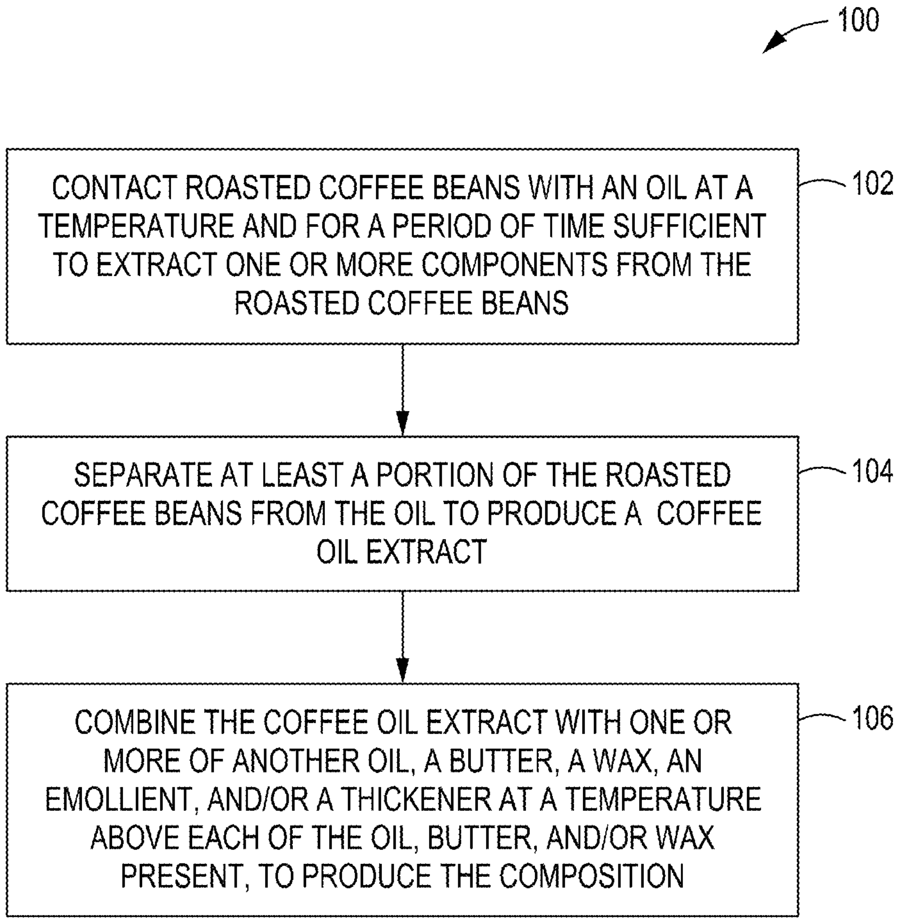
FIG. 1 is a flowchart depicting a method to produce the composition according to embodiments disclosed herein.

Each limitation of an embodiment should be read once as comprising that embodiment, then again as consisting essentially of that embodiment, then again as consisting of that embodiment, unless otherwise indicated. For brevity, the term comprising is used throughout unless otherwise indicated. For purposes herein, the term "about" indicates +/−2% unless otherwise indicated.

The following definitions are provided in order to aid those skilled in the art in understanding the detailed description.

As used herein, the term fatty acid refers to a carboxylic acid having greater than or equal to about 6 carbon atoms. For purposes herein, an oil comprising various fatty acids refers to the fatty acids being present as both free acids, salts, esters, and as mono, di, or triglycerides, according to commonly understood conventions in the art.

As used in the specification and claims, an all-natural material or product is free from synthetic or wholly synthetic, man-made materials. However, for purposes herein, all-natural materials may be purified, separated, and/or processed by "man-made" processes. For example, magnesium hydroxide $Mg(OH)_2$, occurs in nature as the mineral brucite, is produced from MgO sourced from periclase, or produced via treating seawater with lime ($Ca(OH)_2$). While magnesium hydroxide requires processing in the form of purification and separation, magnesium hydroxide and similarly obtained materials are considered to be all-natural materials for purposes herein.

In other examples, coconut oil is a mixture comprising various triglycerides and fatty acids, typically comprising about 90% saturated and 9% unsaturated fatty acids, wherein greater than about 50% of the fatty acids are medium chain fatty acids having 12 carbons or higher. For example, coconut oil typically comprises about 8 wt % caprylic acid C-8:0, 7 wt % capric acid C-10:0, 49 wt % lauric acid C-12:0, 8 wt % myristic acid C-14:0, 8 wt % palmitic acid C-16:0, 2 wt % stearic acid C-18:0, 6 wt % oleic acid C-18:1, and 2 wt % linoleic acid C-18:2. In contrast, fractionated coconut oil is purified, typically by the man-made process of fractional distillation, to produce a composition having about 60 wt % caprylic acid C-8:0 and 40 wt % capric acid C-10:0, with less than about 5 wt % of C12 and higher fatty acids. For purposes herein, fractionated coconut oil is considered an all-natural product, since the starting material is a natural product, which is simply purified or separated, without significantly altering the chemical properties of the individual components.

As used herein, the "oil extract of roasted coffee beans" is also referred to herein as a "coffee oil extract." Unless otherwise noted, both terms are used interchangeably herein. Likewise, the term "synthetic coffee oil extract" refers to a mixture comprising a plurality of compounds known to be present in roasted coffee disposed in an oil carrier or solvent. Compounds known to be present in roasted coffee are readily determined via various literature references. See for example, Saud, Shah et al. "Relationship between the Chemical Composition and the Biological Functions of Coffee" Molecules (Basel, Switzerland), vol. 26, no. 24, 2021, pp. 7634-7647, https://doi.org/10.3390/molecules26247634, last visited Dec. 3, 2024; see also Hurtado-Benavides, Andrés et al. "Study of the fatty acid profile and the aroma composition of oil obtained from roasted Colombian coffee beans by supercritical fluid extraction." Journal of Supercritical Fluids 113 (2016): 44-52.

In embodiments, a composition having deodorant properties comprises an oil extract of roasted coffee beans. In embodiments, the oil extract of roasted coffee beans comprises fractionated coconut oil having a concentration of $C_{12}$ or higher fatty acids of less than or equal to about 5 wt %. In embodiments, the composition further comprises a wax. In embodiments, the wax is white beeswax, yellow beeswax, Chinese wax, lanolin, shellac wax, spermaceti, bayberry wax, candelilla wax, carnauba wax, castor wax, esparto wax, Japan wax, jojoba oil wax, ouricury wax, palm wax, rice bran wax, soy wax, tallow tree wax, ceresin wax, montan wax, ozocerite wax, peat wax, or a combination thereof.

In embodiments, the composition further comprises a starch, an oil, a gum, an inorganic salt, a metal oxide, a metal hydroxide, a flour, or a combination thereof.

In embodiments, the composition further comprises cornstarch, wheat starch, potato starch, rice starch, cassava starch, tapioca starch, arrow root starch, or a combination thereof. In embodiments, the composition further comprises a hard coconut oil, agar, alginic acid, sodium alginate, carrageenan, gum arabic, gum ghatti, gum tragacanth, karaya gum, guar gum, locust bean gum, beta-glucan, dammar gum, glucomannan, psyllium seed husk gum, tara gum, gellan gum, xanthan gum, maltodextrin, a wood flower, a husk flour, or a combination thereof.

In embodiments, the composition further comprises fumed silica, titanium oxide, magnesium hydroxide, calcium hydroxide, sodium chloride, potassium chloride, sodium sulfate, magnesium sulfate, or a combination thereof.

In embodiments, the composition further comprises shea butter, capuacu butter, cocoa butter, mahuwa butter, or a combination thereof.

In embodiments, the composition further comprises a fragrance. In embodiments, the fragrance comprises cottonseed oil, lavender essential oil, vanilla oil, cinnamon oil, citronella oil, goji berry fragrance oil, orange oil, mandarin orange oil, apple seed oil, Caribbean teakwood oil, cedar oil, sandalwood oil, juniper oil, nutmeg oil, star anise oil, patchouli oil, rose oil, clove oil, saffron oil, lavender oil, rosemary oil, clary sage oil, lemon oil, peppermint oil, sweet basil oil, bergamot oil, camellia oil (or tea seed oil), blue chamomile oil, catnip oil, bay leaf oil, clementine oil, coffee essential oil, coconut oil, oregano oil, ylang-ylang oil, neroli essential oil, bergamot essential oil, rose petal oil, jasmine essential oil, vetiver essential oil, citrus essential oil, olibanum essential oil, petitgrain oil, sweet orange oil, myrrh essential oil, coriander seed oil, frankincense oil, white musk, ambergris, civet musk, hyraceum, or a combination thereof.

In embodiments, the oil extract of roasted coffee beans is a synthetic coffee oil extract produced synthetically by mixing a plurality of components present in roasted coffee beans with an oil.

In embodiments, the oil extract of roasted coffee beans is formed from plant-based components, e.g., is vegan. In embodiments, the composition is formed from, or in embodiments is predominantly formed from all-natural components. In embodiments, the composition is formed only from all-natural components, and the composition is an all-natural composition, consisting of all-natural components.

In embodiments, the oil extract of roasted coffee beans is formed by extracting roasted coffee beans with fractionated coconut oil having a concentration of $C_{12}$ and higher fatty acids of less than or equal to about 5 wt % prior to extracting the roasted coffee beans, wherein a weight-to-weight ratio of the fractionated coconut oil to the roasted coffee beans is from about 90:10 to about 10:90.

In embodiments, the composition comprises from about 5 wt % to 30 wt % of the oil extract of roasted coffee beans, based on the total amount of the composition.

In embodiments, a method of making a composition having deodorant properties, comprises contacting roasted coffee beans with an oil, which in embodiments is a plant-based oil, at a temperature and for a period of time sufficient to extract one or more components from the roasted coffee beans, and separating at least a portion of the roasted coffee beans from the oil to produce a coffee oil extract; combining the coffee oil extract with one or more of another oil, an emollient such as a butter, a wax, or a thickener at a temperature above each of the another oil, butter, and/or wax present, to produce the composition.

In an alternative embodiment of the method, the coffee oil extract is replaced by a synthetic coffee oil, which is produced synthetically by combining a plurality of the components known to be present in a coffee oil extract when produced according to embodiments disclosed herein, to form the synthetic coffee oil extract, and then utilizing the synthetic coffee extract to produce the composition having deodorant properties according to embodiments disclosed herein.

In embodiments, the thickener comprises a starch, a vegetable gum, an inorganic salt, a metal oxide, a metal hydroxide, a flour, or a combination thereof.

In embodiments, the method further comprises disposing the composition within a form having a shape, and cooling the composition to produce a solid or semi-solid composition in the shape of the form.

In embodiments, the method further comprises addition of one or more fragrances.

In embodiments, a method of producing a coffee oil extract comprises contacting roasted coffee beans with an extraction solvent comprising fractionated coconut oil at a temperature and for a period of time sufficient to extract at least a portion of the roasted coffee beans into the extraction solvent; and separating at least a portion of the roasted coffee beans from the extraction solvent.

In embodiments, the roasted coffee beans are masticated prior to the contacting with the extraction solvent. In embodiments, the extraction solvent is a plant-based oil. In embodiments, the extraction solvent consists essentially of fractionated coconut oil having a concentration of $C_{12}$ and higher fatty acids of less than or equal to about 5 wt %.

In embodiments, a weight-to-weight ratio of the extraction solvent to the roasted coffee beans is from about is from about 90:10 to about 10:90. In embodiments, the weight-to-weight ratio of extraction solvent to coffee beans is about 90:10, or 85:15, or 70:30, or 60:40, to about 10:90, or 15:85, or 30:70, or 40:60, or 50:50, which in embodiments is 23:1 to about 1:18. In embodiments, the contacting roasted coffee beans with the extraction solvent comprising fractionated coconut oil is at a temperature from about 12° C. to about 53° C., for a period of time from about 0.5 hours to 72 hours. In embodiments, the temperature at which the roasted coffee beans are contacted with the extraction solvent is greater than or equal to about 12° C., or greater than or equal to about 21° C., or greater than or equal to about 28° C., or greater than or equal to about 35° C., and less than or equal to about 53° C., or less than or equal to about 45° C., or less than or equal to about 40° C., for a period of time of greater than or equal to about 0.5 hr, or greater than or equal to about 24 hrs., and less than or equal to about 48 hrs., or less than or equal to about 72 hrs.

In another embodiment, a method to produce a synthetic coffee oil extract comprises combining a plurality of components which are known to be present in a coffee oil extract with a mixture of fatty acids, which in embodiments includes caprylic acid and capric acid, to form the synthetic coffee oil. In some of such embodiments, the mixture of fatty acids comprises or is fractionated coconut oil.

In embodiments, the composition having deodorant properties comprises an oil extract of roasted coffee beans, also referred to herein as a coffee oil extract, which comprises both the components present in the oil used to produce the coffee oil extract, and the components extracted from the roasted coffee beans.

In embodiments, the coffee oil extract or the synthetic coffee oil extract, comprises caprylic acid C-8:0, capric acid C-10:0, lauric acid C-12:0, palmitic acid C-16:0; stearic acid C-18:0; oleic acid C-18:1; linoleic acid C-18:2; linolenic acid C-18:3; and arachidic acid C-20:0.

In embodiments, the coffee oil extract or the synthetic coffee oil extract further comprises one or more compounds belonging to the family of furans, pyrazines, ketones, phenols, pyrroles, pyridines, lactones, thiophenes, thiazoles, short chain carboxylic acids having less than 6 carbon atoms, aromatic carboxylic acids, terpenes, sesquiterpenes, diterpenes, and/or flavonoids (polyphenols), flavanols, or a combination thereof.

In embodiments, the coffee oil extract or the synthetic coffee oil extract utilized to produce the composition, and thus the composition itself comprises 1-ethylpyrrole; pyridine; N-methyl pyridine, trigonelline, theobromine, theophylline, nicotinic acid, theacrine (1,3,7,9-tetramethyluric acid), liberine, methyllibetine, thiazole; 1-hydroxy-2-propanone; 2,5-dimethylpyrazine; 2,6-dimethylpyrazine; 2-ethyl-5-methylpyrazine; 2-furancarboxaldehyde; furfuryl formate; 2-methyl-3,5-dimethylpyrazine; furanmethanol acetate; 5-methyl-2-furancarboxaldehyde; 6,7-dihydro-5-methyl-5H-cyclopentapyrazine; 2 furfuryl propionate; 2-formyl-1-methylpyrrole; 2-furfurylfuran; furanmethanol; 1-(6-methyl-2-pyrazole)-1-ethanone; furfuryl alcohol; 2-ethyl-4-methyl-2,5-furandione; 3-methyl-2-butenoic acid; 2-methyl-1H-pyrrole; beta-damascenone; 2-hydroxy-3-methyl-2-cyclopenten-1-one; guaiacol; 2-methoxyphenol; 3-ethyl-2-hydroxy-2-cyclopenten-1-one; 3-hydroxy-2-methyl-4H-pyran-4-one; difurfuryl ether; 2-formylpyrrole; 4-ethylguaiacol; 4-ethyl-2-methoxyphenol; eicosanol; 4-methylphenol; gamma-decalactone; 4-vinylguaiacol; 2-methoxy-4-vinylphenol; 1-furfuryl-2-formyl pyrrole; benzoic acid, or a combination thereof.

In embodiments, the coffee oil extract or the synthetic coffee oil extract utilized to produce the composition comprises greater than or equal to about 0.1 wt % each of one or more of furanmethanol; 2-ethyl-3-methylpyrazine; difurfuryl ether; 2-furfurylfuran; 5-methyl-2-furancarboxaldehyde; furanmethanol acetate; 2-methoxy-4-vinylphenol; 2-furancarboxaldehyde; 4-ethyl-2-methoxyphenol; 2-hydroxy-3-methyl-2-cyclopenten-1-one; or a combination thereof.

In embodiments, the coffee oil extract or the synthetic coffee oil extract utilized to produce the composition comprises one or more of tannic acid, N-methylnicotinic acid, caffeine, catechin, epicatechin, epicatechin gallate, epigallocatechin gallate, delphinidin-3,5-dilucoside, delphinidin-3-(6"-malonyl-glucoside), cyanidin-3-O-glucoside, cyanidin-3-O-rutinoside, kaempferol, kaempferol glucosides, quercetin, quercetin glycosides and glycuronides, quercitrin, isoquercitrin, rutin, hyperoside, luteolin, patuletin, fisetin, myricetin, pigenin, or a combination thereof.

In embodiments, the coffee oil extract or the synthetic coffee oil extract utilized to produce the composition comprises p-hydroxybenzoic acid, vanillic acid, P-coumaric acid, ferulic acid, chlorogenic acid, gentosic acid, protocatechuic acid, sinapic acid, ferulic acid, p-coumaric acid, caftaric acid, one or more O-p-coumaroylquinic acids, one or more caffeoyl-quinides.

In embodiments, the coffee oil extract or the synthetic coffee oil extract utilized to produce the composition comprises one or more of caffeic acid, caffeoylquinic acid, dicaffeoylquinic acid, 3-O-feruloylquinic acid, 3-O-ferulic acid-4-O-coffee acyl quinic acid (3-O-feruloyl-4-O-caffeoylquinic acid), 3-O-coffee acyl-4-O-ferulic acid acyl quinine (3-O-caffeoyl-4-O-feruloylquinic acid), and derivatives thereof.

In embodiments, the coffee oil extract or the synthetic coffee oil extract utilized to produce the composition comprises chlorogenic acid (5-caffeoylquinic acid).

In embodiments, the coffee oil extract or the synthetic coffee oil extract utilized to produce the composition comprises one or more of cafestol or a derivative thereof, cafetsal or a derivative thereof, kahweol or a derivative thereof, atractyligenin or a derivative thereof, and/or ursolic acid or a derivative thereof.

In embodiments, the coffee oil extract or the synthetic coffee oil extract utilized to produce the composition comprises kahweol or a derivative thereof.

In embodiments, a synthetic coffee extract is produced by combining one or more of the compounds present in a coffee oil extract with fractionated coconut oil.

In embodiments, the composition comprises a wax, which in embodiments, is present at from about 5 wt % to about 25 wt %. In embodiments, the composition comprises greater than or equal to about 5 wt %, or greater than or equal to about 7 wt %, or greater than or equal to about 11 wt %, or greater than or equal to about 15 wt %, or greater than or equal to about 17 wt %, and less than or equal to about 21 wt %, or less than or equal to about 23 wt %, or less than or equal to about 25 wt % of the wax, based on a total amount of the composition.

Suitable waxes include all-natural waxes. In embodiments, the wax is, or includes one or more of white beeswax, yellow beeswax, Chinese wax, lanolin, shellac wax, spermaceti, bayberry wax, candelilla wax, carnauba wax, castor wax, esparto wax, Japan wax, jojoba oil wax, ouricury wax, palm wax, rice bran wax, soy wax, tallow tree wax, ceresin wax, montan wax, ozocerite wax, and/or peat wax.

In embodiments, the composition comprising a thickener, which increases the viscosity of the composition. In embodiments, the composition comprises greater than or equal to about 10 wt %, to about 60 wt % of one or more thickeners. Suitable thickeners include both organic and inorganic materials. In embodiments of the composition, the thickener is, or comprises an oil other than the oil present in the coffee oil extract, which may be a "hard oil" having a melting point above 20° C., a starch, a gum, an inorganic salt, a metal oxide, a metal hydroxide, a flour, or a combination thereof. In embodiments, various thickeners may also be selected to function as emollients, stabilizers, and/or the like.

In embodiments, the composition comprises from about 2 wt % to about 15 wt % of another oil, i.e., an oil, or a blend of other oils, in addition to the oil present in the oil extract of roasted coffee beans (e.g., the coffee oil extract) present in the composition, which is different in overall composition than the oil present in the coffee oil extract. For example, the coffee oil extract may be produced using fractionated coconut oil, which is liquid at 20° C., and the other oil in the composition i.e., the "another oil", comprises a hard coconut oil, having a melting point above 20° C. While the fractionated coconut oil has components which are also present in the hard coconut oil, the hard coconut oil includes other longer-chain fatty acids rendering the oil a solid below 20° C. Accordingly, for purposes herein, the two oils are considered to be different from one-another since they are different in overall composition.

In embodiments, the composition comprises greater than or equal to about 2 wt %, or greater than or equal to about 2.5 wt %, or greater than or equal to about 4 wt %, or greater than or equal to about 7 wt %, and less than or equal to about 11 wt %, or less than or equal to about 12 wt %, or less than or equal to about 15 wt %, of the other oil. Suitable oils include natural oils having a melting point above about 20° C., or from about 22° C. to about 35° C., known in the art as "hard oils". Suitable hard oils include hard coconut oils, hard vegetable oils, and the like.

In embodiments, the composition comprises from about 7 wt % to about 45 wt % of a starch. In embodiments, the composition comprises greater than or equal to about 7 wt %, or greater than or equal to about 10 wt %, or greater than or equal to about 15 wt %, or greater than or equal to about 20 wt %, and less than or equal to about 45 wt %, or less than or equal to about 40 wt %, or less than or equal to about 35 wt %, or less than or equal to about 30 wt % of a starch. Suitable starches include cornstarch, wheat starch, potato starch, rice starch, cassava starch, tapioca starch, arrow root starch, also known in the art as arrow root powder, or a combination thereof.

In embodiments, the composition comprises a gum, a flour, or a combination thereof. In embodiments, the composition comprises from about 10 wt % to about 35 wt % of a gum and/or a flour. In embodiments, the composition comprises greater than or equal to about 10 wt %, or greater than or equal to about 20 wt %, or greater than or equal to about 25 wt %, or greater than or equal to about 28 wt %, and less than or equal to about 35 wt %, or less than or equal to about 33 wt %, or less than or equal to about 30 wt % of a gum, a flour, or a combination thereof.

Suitable gums and/or flours include, agar, alginic acid, sodium alginate, carrageenan, gum arabic, gum ghatti, gum tragacanth, karaya gum, guar gum, locust bean gum, beta-glucan, dammar gum, glucomannan, psyllium seed husk gum, tara gum, gellan gum, xanthan gum, maltodextrin, a wood flower, a husk flour, or a combination thereof.

In embodiments the composition comprises an inorganic salt, a metal oxide, a metal hydroxide, or a combination thereof. In embodiments, the composition comprises from about 2 wt % to about 12 wt % of an inorganic salt, a metal oxide, a metal hydroxide, or a combination thereof. In embodiments, the composition comprises greater than or equal to about 2 wt %, or greater than or equal to about 2.5 wt %, or greater than or equal to about 3.5 wt %, or greater than or equal to about 4 wt %, and less than or equal to about 12 wt %, or less than or equal to about 9 wt %, or less than or equal to about 7 wt % of an inorganic salt, a metal oxide, a metal hydroxide, or a combination thereof. Suitable inorganic salts, metal oxides, and/or metal hydroxides, include fumed silica, titanium oxide, magnesium hydroxide, calcium hydroxide, sodium chloride, potassium chloride, sodium sulfate, magnesium sulfate, or a combination thereof.

In embodiments the composition further includes one or more emollients, and/or skin conditioning components, which in embodiments are, or comprise, a natural "butter." In embodiments, the composition comprises from about 15 wt % to about 22 wt % of a butter or other emollient. In embodiments, the composition comprises greater than or equal to about 15 wt %, or greater than or equal to about 16 wt %, or greater than or equal to about 17 wt %, and less than or equal to about 22 wt %, or less than or equal to about 20 wt %, or less than or equal to about 19 wt % of a butter or other emollient. Suitable butters include shea butter, capuacu butter, cocoa butter, mahuwa butter, or a combination thereof.

In embodiments the composition further includes one or more fragrances. In embodiments, the composition comprises from about 0.5 wt % to about 7 wt % of a fragrance. In embodiments, the composition comprises greater than or equal to about 0.5 wt %, or greater than or equal to about 1 wt %, or greater than or equal to about 3 wt %, and less than or equal to about 7 wt %, or less than or equal to about 6 wt %, or less than or equal to about 5 wt % of a fragrance. Suitable fragrances include cottonseed oil, lavender essential oil, vanilla oil, cinnamon oil, citronella oil, goji berry fragrance oil, orange oil, mandarin orange oil, apple seed oil, Caribbean teakwood oil, cedar oil, sandalwood oil, juniper oil, nutmeg oil, star anise oil, patchouli oil, rose oil, clove oil, saffron oil, lavender oil, rosemary oil, clary sage oil, lemon oil, peppermint oil, sweet basil oil, bergamot oil, camellia oil (or tea seed oil), blue chamomile oil, catnip oil, bay leaf oil, clementine oil, coffee essential oil, coconut oil, oregano oil, ylang-ylang oil, neroli essential oil, bergamot essential oil, rose petal oil, jasmine essential oil, vetiver essential oil, citrus essential oil, olibanum essential oil, petitgrain oil, sweet orange oil, myrrh essential oil, coriander seed oil, frankincense oil, white musk, ambergris, civet musk, hyraceum, or a combination thereof.

FIG. 1 is a flowchart depicting a method 100 of making a composition having deodorant properties. The method 100 comprises contacting roasted coffee beans with an oil at a temperature and for a period of time sufficient to extract one or more components from the roasted coffee beans [block 102]; separating at least a portion of the roasted coffee beans from the oil to produce a coffee oil extract [block 104]; combining the coffee oil extract with one or more of another oil, a butter, a wax, an emollient, and/or a thickener at a temperature above each of the oil, butter, and/or wax present, to produce the composition [block 106]. The thickener may be a starch, an oil other than the oil present in the coffee oil extract, a gum, an inorganic salt, a metal oxide, a metal hydroxide, a flour, or a combination thereof, according to embodiments disclosed herein.

Examples

A coffee extract was prepared according to embodiments disclosed herein and analyzed via GC/MS to determine the presence of various components of the coffee extract prior to being formulated into the deodorant composition.

A coffee extract was produced using roasted Arabica coffee beans. The roasted coffee beans were ground and then extracted with a fractionated coconut oil composition at a temperature below about 50° C. for about 24 hours. The extract was then filtered to remove the roasted coffee bean solids to produce a slightly turbid coffee extract having a brown color.

A control sample of the fractionated coconut oil composition used to produce the coffee extract, and a sample comprising the coffee extract were then dissolved in DMC and analyzed via GC/MS (DB-3, 30 m, 30° C.-5 min, ramp@20C/min–285° C. hold 15 min, EI(+) scanning 10-400 m/z).

The GC/MS analysis of the coffee extract confirmed the presence of caprylic acid (C8) and capric acid (C10) present in both the fractionated coconut oil control sample and the coffee oil extract. The fatty acid content of both the control sample and the coffee extract was subsequently verified via HPLC/UV analysis.

Figure 2:
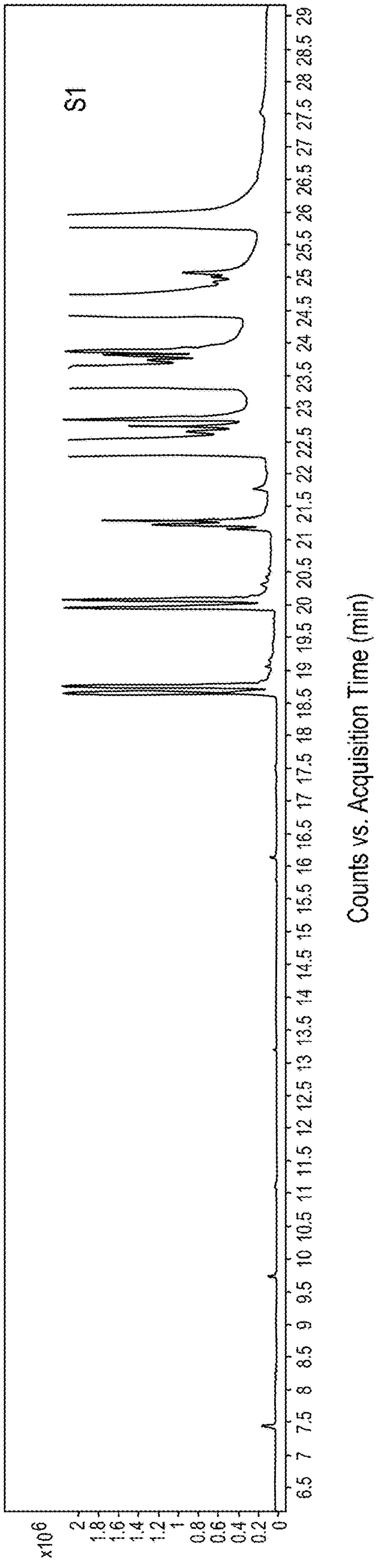
FIG. 2 is a gas chromatogram showing an analysis of a fractionated coconut oil control sample.
Figure 3:
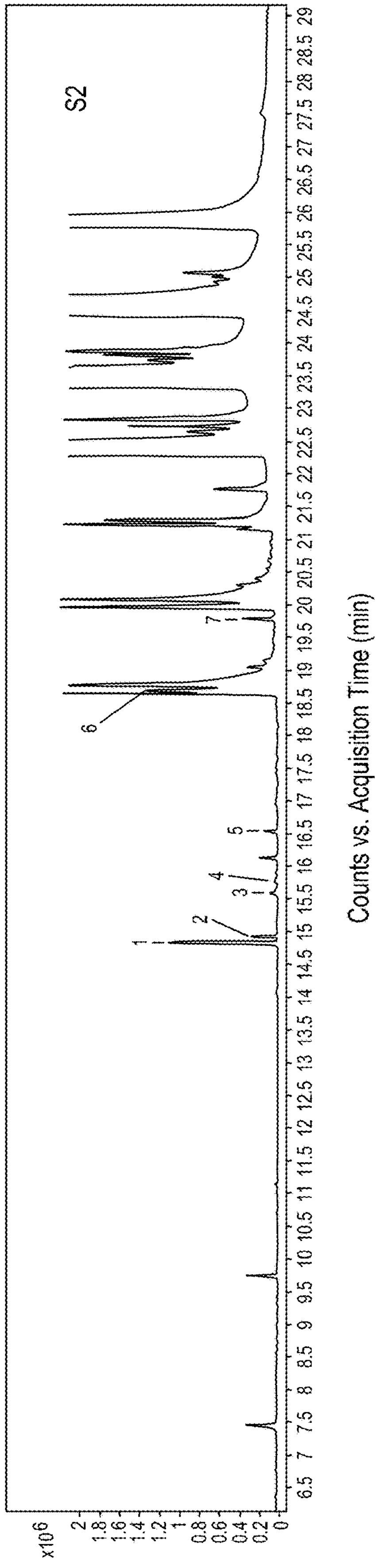
FIG. 3 is a gas chromatogram showing an analysis of coffee oil extract according to embodiments disclosed herein.

FIG. 2 depicts a portion of a gas chromatogram from the analysis of the fractionated coconut oil composition control sample. FIG. 3 depicts a corresponding portion of a gas chromatogram from the analysis of an inventive coffee oil extract, indicating a number of compounds extracted from the roasted coffee beans into the fractionated coconut oil to form the inventive coffee oil extract. The compounds identified by peak number in FIG. 3 have a relatively higher vapor pressure than the vapor pressure of the components present in the fractionated coconut oil composition. Compounds known to be present in roasted coffee beans having a vapor pressure similar to or lower than the components of the fractionated coconut oil are thought to be obscured by the components of the fractionated coconut oil.

Mass spectral analysis of the various compounds identified by numbered peak in the gas chromatogram are shown in Table 1.

TABLE 1

| Peak No. | RT (min) | Identification |
|---|---|---|
| 1 | 14.83 | Caffeine |
| 2 | 14.93 | Fatty Acid Ester |
| 3 | 15.60 | Hexadecanoic acid |
| 4 | 15.76 | Fatty acid ester |
| 5 | 16.54 | Nonyl decanoate |
| 6 | 18.69 | Dioctanoin |
| 7 | 19.78 | Kahweol derivative |

Figure 4:
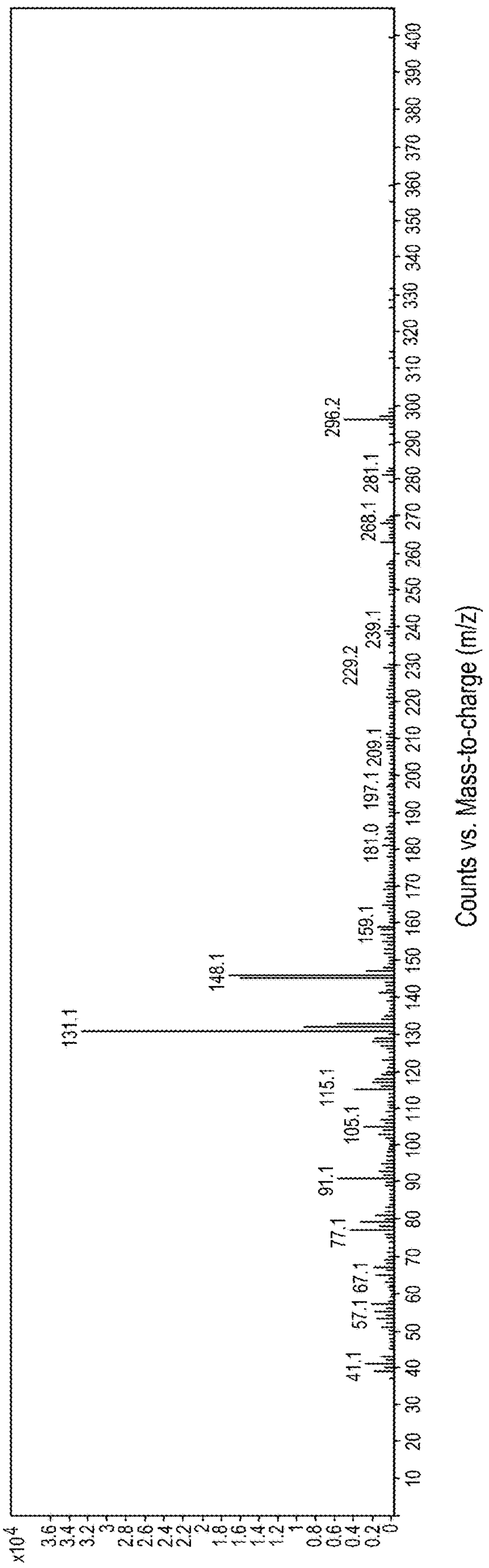
FIG. 4 is a mass spectrum of a component identified in the gas chromatogram shown in FIG. 3.

FIG. 4 is a mass spectrum of Peak 7 of the above Table 1, which is consistent with a kahweol derivative, indicative of the terpene and flavonoid content known to be present in roasted coffee beans, and which is present in the inventive coffee oil extract. This inventive coffee oil extract is then subsequently incorporated into the final composition.

While the foregoing is directed to embodiments of the present disclosure, other and further embodiments of the disclosure may be devised without departing from the basic scope thereof.

The invention claimed is:

1. A composition having deodorant properties, comprising: an oil extract of roasted coffee beans resultant from roasted coffee beans extracted with an oil.

2. The composition of claim 1, wherein the oil of the oil extract of roasted coffee beans comprises fractionated coconut oil having a concentration of $C_{12}$ or higher fatty acids of less than or equal to about 5 wt %.

3. The composition of claim 1, further comprising a wax.

4. The composition of claim 3, wherein the wax is white beeswax, yellow beeswax, Chinese wax, lanolin, shellac wax, spermaceti, bayberry wax, candelilla wax, carnauba wax, castor wax, esparto wax, Japan wax, jojoba oil wax, ouricury wax, palm wax, rice bran wax, soy wax, tallow tree wax, ceresin wax, montan wax, ozocerite wax, peat wax, or a combination thereof.

5. The composition of claim 1, further comprising a starch, an oil different from the oil used to extract the roasted coffee beans, a gum, an inorganic salt, a metal oxide, a metal hydroxide, a flour, or a combination thereof.

6. The composition of claim 1, further comprising cornstarch, wheat starch, potato starch, rice starch, cassava starch, tapioca starch, arrow root starch, or a combination thereof.

7. The composition of claim 1 further comprising a hard coconut oil, agar, alginic acid, sodium alginate, carrageenan, gum arabic, gum ghatti, gum tragacanth, karaya gum, guar gum, locust bean gum, beta-glucan, dammar gum, glucomannan, psyllium seed husk gum, tara gum, gellan gum, xanthan gum, maltodextrin, a wood flower, a husk flour, or a combination thereof.

8. The composition of claim 1, further comprising fumed silica, titanium oxide, magnesium hydroxide, calcium hydroxide, sodium chloride, potassium chloride, sodium sulfate, magnesium sulfate, or a combination thereof.

9. The composition of claim 1, further comprising shea butter, capuacu butter, cocoa butter, mahuwa butter, or a combination thereof.

10. The composition of claim 1, further comprising a fragrance comprising one or more of cottonseed oil, lavender essential oil, vanilla oil, cinnamon oil, citronella oil, goji berry fragrance oil, orange oil, mandarin orange oil, apple seed oil, Caribbean teakwood oil, cedar oil, sandalwood oil, juniper oil, nutmeg oil, star anise oil, patchouli oil, rose oil, clove oil, saffron oil, lavender oil, rosemary oil, clary sage oil, lemon oil, peppermint oil, sweet basil oil, bergamot oil, camellia oil, blue chamomile oil, catnip oil, bay leaf oil, clementine oil, coffee essential oil, coconut oil, oregano oil, ylang-ylang oil, neroli essential oil, bergamot essential oil, rose petal oil, jasmine essential oil, vetiver essential oil, citrus essential oil, olibanum essential oil, petitgrain oil, sweet orange oil, myrrh essential oil, coriander seed oil, frankincense oil, white musk, ambergris, civet musk, hyraceum, or a combination thereof.

11. The composition of claim 1, wherein the oil extract of roasted coffee beans is formed from all-natural components.

12. The composition of claim 1, wherein the oil extract of roasted coffee beans-is formed by extracting the roasted coffee beans with fractionated coconut oil having a concentration of $C_{12}$ and higher fatty acids of less than or equal to about 5 wt % prior to extracting the roasted coffee beans, wherein a weight-to-weight ratio of the fractionated coconut oil to the roasted coffee beans is from about 90:10 to about 10:90.

13. The composition of claim 1, comprising from about 5 wt % to 30 wt % of the oil extract of roasted coffee beans, based on a total amount of the composition.

14. A method of producing a coffee oil extract, comprising:

masticating a plurality of roasted coffee beans;

contacting the masticated roasted coffee beans with an extraction solvent comprising fractionated coconut oil at a temperature from about 12° C. to about 53° C., and for a period of time from about 0.5 hours to 72 hours; and separating at least a portion of the masticated roasted coffee beans from the extraction solvent.

15. The method of claim 14, wherein the extraction solvent consists essentially of fractionated coconut oil having a concentration of $C_{12}$ and higher fatty acids of less than or equal to about 5 wt %.

16. The method of claim 14, wherein a weight-to-weight ratio of the extraction solvent to the roasted coffee beans is from about 90:10 to about 10:90.

* * * * *